United States Patent [19]

Yoshihara et al.

[11] 4,180,857
[45] Dec. 25, 1979

[54] APPARATUS FOR PROCESSING CHROMATOGRAPH DATA

[75] Inventors: Touhachi Yoshihara; Koji Nishiwaki; Kiwao Seki, all of Katsuta, Japan

[73] Assignee: Hitachi, Ltd., Japan

[21] Appl. No.: 811,139

[22] Filed: Jun. 28, 1977

[30] Foreign Application Priority Data

Jun. 30, 1976 [JP] Japan ............................... 51-76348

[51] Int. Cl.$^2$ .................... G06F 15/20; G06K 15/10
[52] U.S. Cl. ..................................... 364/497; 364/519
[58] Field of Search ... 364/497, 498, 519, 200 MS File, 364/900 MS File; 73/23, 23.1; 356/81

[56] References Cited

U.S. PATENT DOCUMENTS

| | | | |
|---|---|---|---|
| 3,562,501 | 2/1971 | Mears | 73/23 |
| 3,721,813 | 3/1973 | Condon et al. | 364/200 |
| 3,818,197 | 6/1974 | Piccolo et al. | 356/81 |
| 3,986,011 | 10/1976 | Poole et al. | 364/200 |

OTHER PUBLICATIONS

Briggs: Computer—Controlled Chromatographs Control Engineering vol. 14, No. 9, Sep. 1967, pp. 75/80.

*Primary Examiner*—Felix D. Gruber

*Attorney, Agent, or Firm*—Craig and Antonelli

[57] ABSTRACT

The data processing apparatus according to this invention comprises a microprocessor and a dot printer. The printer is of such a type that the printing paper is stepwise advanced each time a line of characters are printed. The analog signal from the detector of a chromatograph is converted to a corresponding digital signal. A block of data values to be printed on one line, separated from the digital signal corresponding to the waveform pattern varying with time, is stored in a print buffer memory. The stored data values are printed out in dot matrix form. The emptied buffer memory then stores another block of data values to be plotted on the next line. Thereafter, the plotting and storing operations are repeated until a chromatogram is completed. The concentrations of the components corresponding to the peaks of the chromatogram are also calculated by processing the digital signal and the result of the calculation is printed out in the form of characters each composed of plural dots by the same printer. Thus, the chromatogram consisting of the respective component peaks and the annotating characters representing the calculated concentrations of the components can be printed on the same paper by the same printing means.

6 Claims, 6 Drawing Figures

APPARATUS FOR PROCESSING CHROMATOGRAPH DATA

BACKGROUND OF THE INVENTION

This invention relates to a method and an apparatus for processing data, especially adapted to process the analog data available from chemical analyzing apparatus or the like and to display the result of the processing in both figures and characters.

The analyzing apparatus for obtaining the information on the components contained in a sample to be examined, often detects the peaks appearing with the lapse of time. One example is a chromatograph. In a conventional chromatography the areas under the component peaks of the chromatogram are obtained by integrating the analog signal from the detector, the concentrations of the components are calculated according to the obtained areas and the result of the calculation is printed on the rolled paper. On the other hand, the waveform as chromatogram is plotted on a chart paper. Accordingly, the rolled paper and the chart paper must be inspected together when the usable information is required.

The Japanese Laid-Open Patent Publication (Kokai) No. 12796/73 discloses a prior art apparatus which is an improvement on the display system in which a transparent tape is used for characters, the speed of advance of this transparent tape is set equal to that of the chart paper, and the tape carrying thereon the result of the calculation expressed in the form of characters are stuck on the chart having a chromatogram thereon, after the completion of the analysis. With this apparatus, the handling of the final data is indeed facilitated, but there still remains a laboriousness in sticking the transparent tape upon the chart paper with both in proper registration with each other. Moreover, this apparatus needs both a chart recorder and a printer so as to process the data from a chromatograph.

Recently, there has been developed a data processing apparatus for a gas chromatograph, which plots a chromatogram and prints the annotating characters expressing the result of analysis, on the same paper, as disclosed in U.S. Pat. No. 3,986,011 which has been issued after the filing data of the corresponding Japanese Patent Application of this application. However, this apparatus, in which the means for drawing chromatograms is always kept in contact with the paper, has a poor ability to follow up waveforms. Moreover, in this apparatus, the sensitivity cannot be changed while any chromatogram is being drawn, so that if the sensitivity is so set as to be suitable for major components, the peak profiles for minor components cannot be recognized while the sensitivity set suitable for the minor components causes the amplitude of the peak of the major components to be out of scale.

SUMMARY OF THE INVENTION

One object of this invention is to provide a method and an apparatus for processing data, which can display the waveform corresponding to an analog signal and the characters expressing the result of analysis, by substantially the same technique.

Another object of this invention is to provide a method and an apparatus for processing data, which can recognize the peaks of both major and minor components in a mixture sample through a single measurement, the major component having a considerable amount and the minor component having a trace of amount.

Yet another object of this invention is to provide a method and an apparatus for processing data, which can easily display both the waveform corresponding to an analog signal and the characters expressing the result of analysis.

Still another object of this invention is to provide a method and an apparatus for processing data, which does not require remeasurement for confirming the peak profiles and therefore may decrease laboriousness in operation.

According to this invention, the analog signal having a waveform varying with time is converted to a digital signal. The digital signal is successively stored in a memory element having plural bits until all the bits are filled. Accordingly, the memory element stores waveform data corresponding to the analog signal. The stored waveform data is plotted on paper in the form of plural dots by a dot printer. The printed pattern on the paper is substantially the same as the stored waveform data. The stored data has a length to be printed out during one excursion of the printer head from one edge to the other of the paper. After the length of data has been printed out, the memory element stores the data of the same length for the next printing. The operations of storing and printing are repeated. On the other hand, the digital signal is also subjected to an arithmetic operation according to a stored program and thereafter printed out as characters in dot matrix form by the same printer.

Other objects and features of this invention will be apparent from the following description of a preferred embodiment.

DETAILED DESCRIPTION OF THE PREFERRED EMBODIMENT

Figure 1:
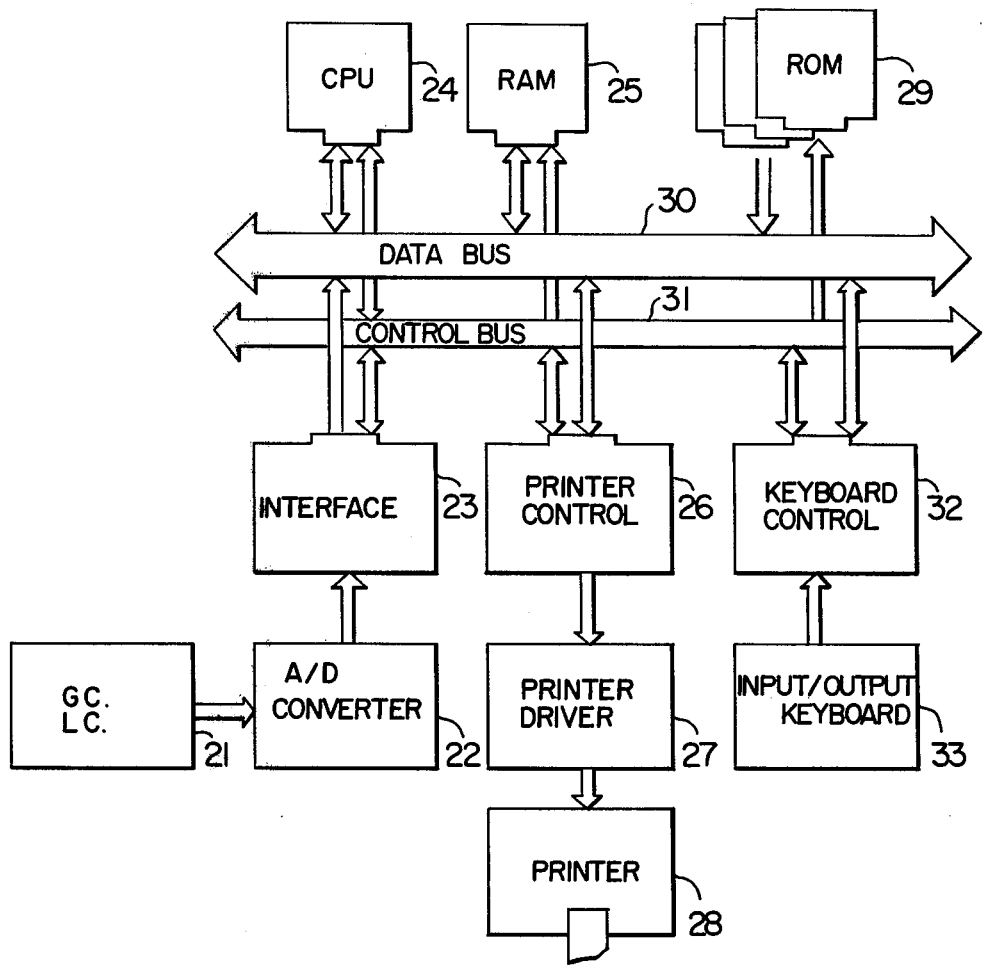
FIG. 1 shows in block diagram a data processing apparatus as an embodiment of this invention.

An embodiment of this invention is shown in FIG. 1 by way of block diagram. The data processing apparatus shown in FIG. 1 can be connected with a gas chromatographer (GC) or a liquid chromatographer (LC) to serve as an analog signal source 21. The mechanism for converting the analog signal to a digital one is not limited to an analog-digital (A-D) converter 22 connected between the analog signal source 21 and an interface 23, but a V-F converter may be provided instead of the A-D converter 22 in the same place to obtain a digital signal in cooperation with a central processor unit.

The interface 23 is connected with a central processor unit (CPU) 24 through a data bus 30 and a control bus 31. As the CPU 24 is used a 16-bit microprocessor.

As memories are employed a RAM 25 and a ROM 29. An operation console, including an input/output keyboard 33 and a keyboard control 32, can generate functions, deliver numerical values and display numerical values.

A printer control 26 controls through a printer driver 27 a printer 28 which can produce a chromatogram on a plotting paper. As the printer 28, a high-speed printer of dot matrix type having an inked ribbon may be used, e.g. a mosaic printer manufactured by Philips Co. This high-speed printer has a diode matrix and characters are printed out in dot matrix form, 7 rows by 5 columns. The print head has 7 needles serving as print segments and each character is formed by causing the needles to press against the inked ribbon. One excursion of the print head from one edge to the other of the printing paper corresponds to a line of 20 characters, printed out in a second. Another suitable printer is, for example, a thermal printer (heat-sensitive type) disclosed in the Japanese Laid-Open Patent Publication (Kokai) No. 62150/74. This printer has a plurality of resistive elements arranged linearly on its print head and characters are printed in matrix fashion, 7 rows by 5 columns. To complete the print-out of one character, the heat-sensitive paper is advanced seven times stepwise.

Figure 2:
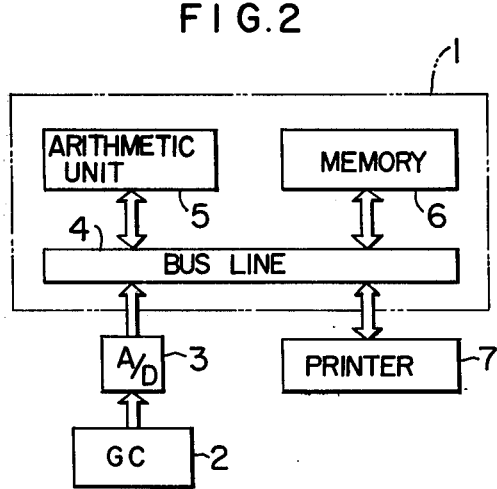
FIG. 2 shows in block diagram a simplified version of the data processing apparatus shown in FIG. 1, suitable to make the explanation concise.

FIG. 2 is a simplified version of FIG. 1. A data processing unit 1 incorporates therein a bus line 4, an arithmetic unit 5 and a memory 6. In a gas chromatograph system 2, the components contained mixed in a sample to be tested are separated from one another in a separating column and consecutively arrive at detectors. The analog signal delivered from the detectors of the gas chromatograph 2 is a waveform consisting of successive peaks appearing with time and the area under each peak corresponds to the quantity of the associated component. The analog signal is sent to an A-D converter 3 and the output digital signal of the A-D converter 3, is delivered onto the bus line 4. The digital signal is then processed by the arithmetic unit 5 and the processed data is stored at predetermined locations in the memory 6. As the analysis using the gas chromatograph proceeds, the four differently attenuated versions of the original digital signal are successively taken into the memory locations in such a manner that each version has a pattern substantially resembling the waveform of the corresponding analog signal. When all such memory locations are filled, the stored patterns are printed out in dot form on a printing or plotting paper.

When a peak has appeared in the chromatogram, the arithmetic unit 5 performs the calculation for obtaining the concentration of the component corresponding to the peak, on command by the stored program and the obtained concentration and the retention time etc. are stored in the memory 6. After all the peaks required have been plotted as a completed chromatogram on the plotting paper, the result of the calculation is dotprinted by a printer 7 on the same paper.

The memory 6 has, besides the above mentioned locations for the digital signals and the result of calculations, a print buffer section and a data area.

Figure 3:
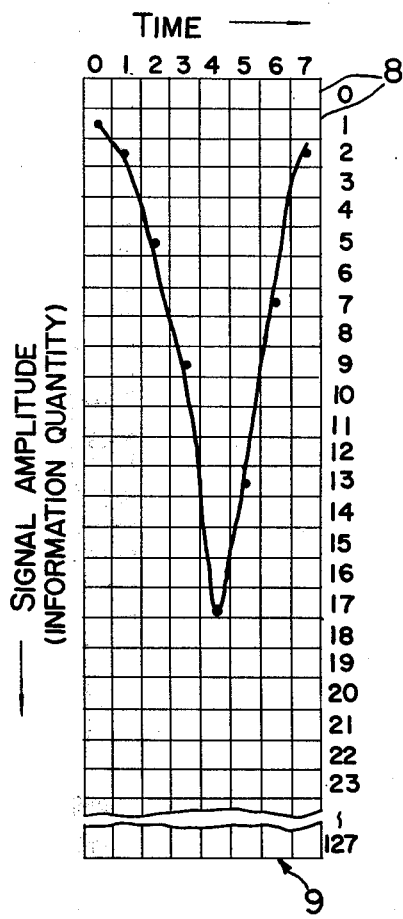
FIG. 3 illustrates the distributed states of the data values in the print buffer memory.

FIG. 3 schematically shows the state of the data values, i.e. digital signal, distributed in the print buffer section. The print buffer section 9 temporarily stores a block of data values to be plotted during one execursion of the print head from one edge to another of the plotting paper. The print buffer section 9 consists of 128 8-bit data memory elements 8. A first digital data value obtained through integration over a certain constant, very short time duration is registered into the leftmost column #0. When the next digital data value comes in, the first digital data value already stored in the column #0 is shifted to the column #1 so as to enable the second input data value to be registered into the column #0. In the same manner, the successive data values are registered consecutively into the columns #2, #3, etc. When the print buffer section 9 is filled in this manner with data values, the arithmetic unit 5 in FIG. 2 commands the printer 7 to plot on the plotting paper the data values in the order in which they are registered into the print buffer section 9. The dots shown in the development of the print buffer section 9 in FIG. 3 represent the stored location of the respective data values. The curve obtained by connecting the dots with lines resembles the peak waveform of the corresponding component.

In a practical gas chromatography, the sampling time for the data values filling the print buffer section 9 is very much shorter than the time for elution of any component peak and therefore the stored pattern in the section 9 is almost linear, different from the pattern shown in FIG. 3 exaggerated for facilitating the understanding of the function of the print buffer section 9. The data values temporarily stored in the section 9 are replaced, after they have been plotted, by another block of data values for next plotting in the same order as described above. These operations of storing and plotting are repeated until a predetermined time is reached.

Figure 4:
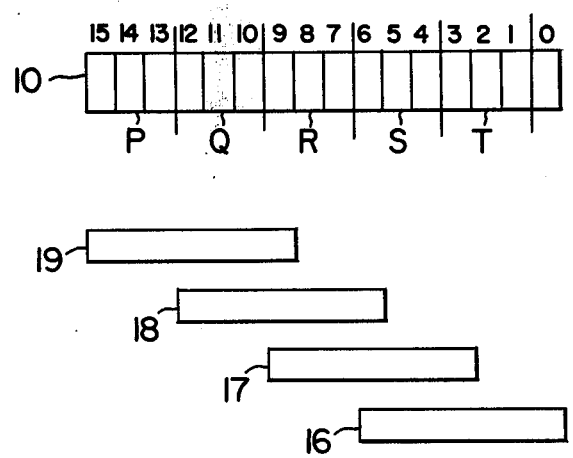
FIG. 4 illustrates how data values having different amplitudes are obtained in the memory.

FIG. 4 illustrates how differently attenuated signals are obtained in the memory. The digital signal from the A-D converter 3 passes through the data area 10 in the memory 6 before it reaches the print buffer section 9. When the digital signal enters the data area having 16 bits, the signal is divided into 5 ranges, i.e. P, Q, R, S and T ranges, each range having 3 bits. When the bit ranges corresponding to masking 19 are checked, the non-attenuated data values are sent to the print buffer section 9. When the bit ranges corresponding to the masking 18 are checked, the data values attenuated by a factor of $\frac{1}{8}$ are delivered to the section 9. In a like manner, the maskings 17 and 16 corresponds respectively to the attenuation factors of (1/64) and (1/512).

Figure 5:
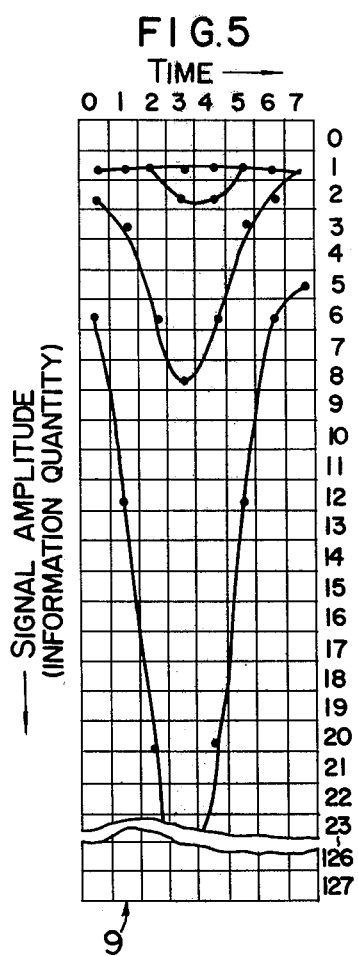
FIG. 5 illustrates the states of the data values having small amplitudes.

FIG. 5 shows how the attenuated signals are stored in the print buffer section 9. The data values sent from the data area 10 of FIG. 4 are sequentially stored in the print buffer section 9, as shown in FIG. 5. The waveform patterns having different amplitudes corresponding to the different attenuation factors are distributed. When the print buffer section 9 is filled, the print head of the printer 7 plots on the paper patterns corresponding to those stored in the section 9, while shifting perpendicularly to the direction in which the paper is advanced. When the print head completes an excursion from one edge to the other, the data values stored in the section 9 and used for the plotting are erased, and the data values for forming the waveforms for the next plotting are registered in the print buffer section 9. Upon completion of each excursion of the print head, the plotting paper is stepwise advanced by a small distance. For the simplicity of structure, the speed of the stepwise advance may be kept constant in both plotting the chromatogram and printing the annotating characters. The distance between the dots printed by the print head remains the same in either plotting the chromatogram or printing the annotating characters, but in the case of printing characters a blank line is interposed between one line of characters and another.

In this embodiment, there may be provided two print buffer sections and in a period when one of the two print buffer sections is in a state that the signals stored in the one print buffer section are transferred to the dot printer, the other print buffer section is kept in the state storing the digital signals. Thus, the digital signals may be stored alternately and alternatively in the two print buffer sections, it is possible to continuously store the digital signals. Three or more print buffer sections may of course be provided.

Figure 6:
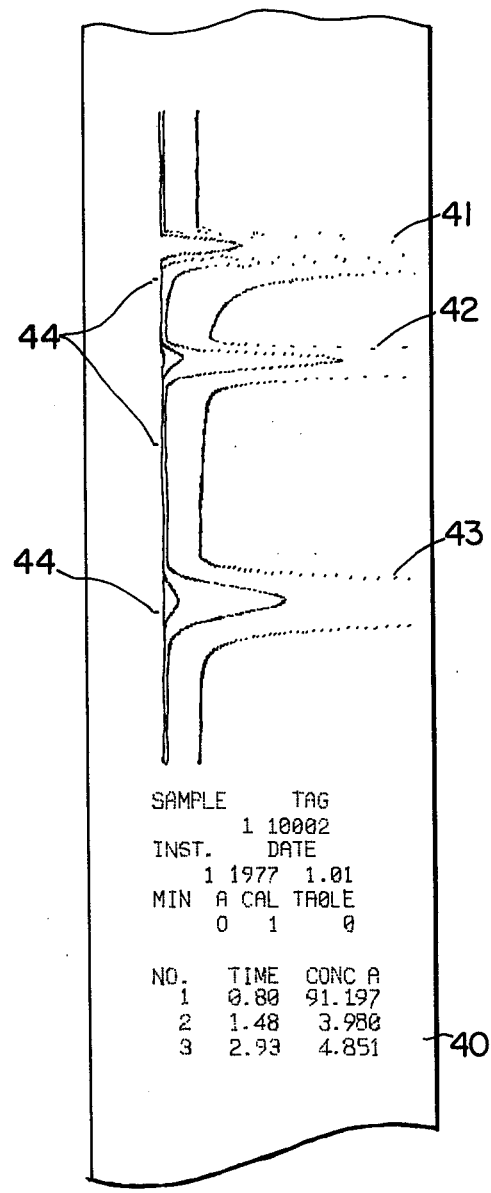
FIG. 6 shows an example of the information plotted and printed out according to this invention.

FIG. 6 shows an example of an analyzed information obtained by the data processing apparatus according to this invention. The analyzed sample is a mixture of benzene, toluene and xylene. The peaks of the respective components, attenuated according to the four different attenuation factors, are plotted on the paper. While the shape of the peak 41 of benzene which is a major component, can be recognized in the case of the attenuation by a factor of (1/512,) it cannot be examined under the other attenuation factors since the peak is there too high, i.e. out of scale. The peaks 42 and 43 corresponding respectively to toluene and xylene which are by far smaller in quantity than benzene, can be recognized in the case of the attenuation by a factor of ($\frac{1}{8}$). For components having even smaller quantities, the analysis is performed on the non-attenuated peaks. In this way, the peaks of both the major and minor components can be examined at a time.

The amplitude axis of the chromatogram is arranged substantially parallel to the lines of characters.

On the plotting and printing paper 40 are printed the condition of analysis by the gas chromatograph and the concentrations of respective components. "NO" gives the order number of the peaks appearing with time. "TIME" represents the retention times of the respective peaks. "CONC A" indicates the percentages of the respective components in the initial mixture.

In FIG. 6, the equi-spaced dots 44 below the base line are marked at a predetermined interval starting from the time when a sample is brought into a gas chromatograph apparatus. In FIG. 6, the dots are marked at an interval of one minute.

As described above, according to this invention, both the figure, as a chromatogram, corresponding to the analog signal and the annotating characters as the result of calculation can be displayed on a sheet of paper so that the manipulation of the analysis can be facilitated.

The application of this invention is by no means limited to the embodiment described above, but the data processing apparatus according to this invention is suitable to process the data derived from the liquid chromatogram, the mass spectrograph and other types of analyzers.

We claim:

1. A data processing apparatus comprising:
   means for converting to digital signals an analog signal which is generated by an analog signal generating source and varies with time;
   arithmetic means for subjecting said digital signals to an arithmetic operation according to a stored program;
   memory means for storing the result of said arithmetic operation, said memory means including a print buffer memory which successively stores in its plural bit locations the digital signals as a figure in general corresponding to said analog signal;
   dot printer means for printing out on paper input signals in the form of plural dots, said printer means including a print head carrying thereon a plurality of print segments; and
   means for controlling said printer means to act in a manner so that after said bit locations of said buffer memory has been filled with the digital signals as a figure in general corresponding to said analog signal, the digital signals filling said bit locations are displayed corresponding to said figure in the form of plural dots on said paper by successively actuating a plurality of the print segments and that said result of said arithmetic operation is printed out as characters in rows each being in dot matrix form.

2. A data processing apparatus as claimed in claim 1, wherein said analog signal source is a chromatograph apparatus and said figure printed out on said paper is a chromatogram.

3. A data processing apparatus as claimed in claim 2, wherein the direction of amplitude of said chromatogram is substantially parallel to said rows of characters.

4. A data processing apparatus as claimed in claim 1, wherein said control means causes said printer to print out said result of said arithmetic operation after the figure corresponding to the entire analog signal has been displayed.

5. A data processing apparatus comprising:
   means for converting to digital signals an analog signal which is generated by an analog signal generating source and varies with time;
   arithmetic means for subjecting said digital signals to an arithmetic operation according to a stored program;
   memory means for storing the result of said arithmetic operation, said memory means including a print buffer memory which successively stores in its plural bit locations the digital signals as a figure in general corresponding to said analog signal, said memory means including means for obtaining plural attenuated digital signals by attenuating each of said digital signals every time it is received according to plural attenuating factors before said digital signals have been transferred to said print buffer memory;
   dot printer means for printing out on paper input signals in the form of plural dots, said printer means including a print head carrying thereon a plurality of print segments; and
   means for controlling said printer means to act in a manner so that after said bit locations of said buffer memory has been filled with the attenuated digital signals as a figure in general corresponding to said analog signal, the attenuated digital signals filling said bit locations are displayed corresponding to said figure in the form of plural dots on said paper by successively actuating a plurality of the print segments and that said result of said arithmetic operation is printed out as characters in rows each being in dot matrix form.

6. A data processing apparatus for printing a chromatogram having a plurality of reduced graphs comprising:
   means for converting to digital signals an analog signal which is generated by a chromatograph apparatus and varies with time;
   arithmetic means for subjecting said digital signals to an arithmetic operation according to a stored program to calculate the component concentrations from the chromatograph;

memory means for storing the result of said arithmetic operation, said memory means including a print buffer memory which successively stores in its plural bit locations the digital signals as a figure in general corresponding to said analog signals, said memory means including means for obtaining plural attenuated digital signals by attenuating each of said digital signals every time it is received according to plural attenuating factors before said digital signals have been transferred to said print buffer memory;

dot printer means for printing out on paper input signals in the form of plural dots, said printer means including a print head carrying thereon a plurality of print segments; and means for controlling said printer means to act in a manner so that after said bit locations of said buffer memory has been filled with the attenuated digital signals as a figure in general corresponding to said analog signals, the attenuated digital signals filling said bit locations are displayed as a plurality of reduced graphs corresponding to said figure in the form of plural dots on said paper by successively actuating all the print segments as the print head is moved in one direction across the paper, and that component concentrations are printed out as characters in rows each being in dot matrix form.

* * * * *